United States Patent [19]  [11] 3,980,718
Shabtai et al.  [45] Sept. 14, 1976

[54] PRODUCTION OF ALCOHOLS BY REDUCTION OF CARBONYL COMPOUNDS WITH A CRYSTALLINE ALUMINOSILICATE-ISOPROPANOL SYSTEM

[75] Inventors: Joseph Shabtai, Rehovot, Israel; Gerhard Martin Julius Schmidt, deceased, late of Rehovot, Israel, by Ester Schmidt, executrix

[73] Assignee: Yeda Research & Development Co. Ltd., Rehovot, Israel

[22] Filed: Jan. 10, 1972

[21] Appl. No.: 216,767

[30] Foreign Application Priority Data
Jan. 13, 1971  Israel...................................... 35994
June 16, 1971  Israel...................................... 37077

[52] U.S. Cl. .......................... 260/631.5; 260/631 R; 260/638 B; 252/455 Z
[51] Int. Cl.² ................... C07C 47/20; C07C 47/02
[58] Field of Search ...................... 260/631.5, 638 B

[56] References Cited
UNITED STATES PATENTS
2,117,463   5/1938   Terwilliger........................ 260/631.5
2,767,221  10/1956   Ballard et al..................... 260/638 B FOREIGN PATENTS OR APPLICATIONS
938,479   9/1948   France ............................ 260/638 B
740,641   1/1933   France ............................ 260/638 B

OTHER PUBLICATIONS

Venuto, "Advances in Chemistry Series," No. 102, pp. 271–281, Amer. Chem. Soc., Wash., D.C., (1971).

Kunichika et al., "Chem. Abstracts," vol. 66, par. 283352, (1967).

Malinowski et al., "Chemical Abstracts," vol. 56, p. 973i, (1962).

*Primary Examiner*—Paul M. Coughlan, Jr.
*Assistant Examiner*—D. B. Springer
*Attorney, Agent, or Firm*—Ostrolenk, Faber, Gerb & Soffen

[57] ABSTRACT

Aliphatic alcohols are producted by reducing the corresponding aldehydes and ketones by contact with a molecular sieve zeolite having adsorbed therein a secondary alcohol which acts as a hydrogen donor agent.

12 Claims, No Drawings

PRODUCTION OF ALCOHOLS BY REDUCTION OF CARBONYL COMPOUNDS WITH A CRYSTALLINE ALUMINOSILICATE-ISOPROPANOL SYSTEM

This invention relates to the production of saturated and unsaturated alcohols. The invention provides a convenient, high-yield process for the manufacture of primary and secondary alcohols by reduction of aldehydes and ketones with a novel hydrogen transfer system. Fundamentally, the latter is a two-component system, which consists of (1) a molecular sieve zeolite (crystalline aluminosilicate) possessing an appropriate pore size and geometry, and (2) a suitable hydrogen-donor ingredient.

The aluminosilicate component of the reducing system employed in the process of this invention preferably belongs to the faujasite family of zeolites. It is a requirement of the process that the aluminosilicate component should have an intracrystalline channel system with a pore diameter of sufficient dimensions to accommodate the carbonyl-containing substrate. For example, type 13X faujasite, with a nominal pore size of 10A, or type 10X faujasite, with a nominal pore size of 8A, can be conveniently employed as components of the reducing system used in the process of this invention for production of saturated alcohols. Other crystalline aluminosilicates, e.g. Y-type faujasites, mordenites, etc., which possess a channel system with similar or somewhat different pore sizes, may likewise be used as components of the reducing system.

Isopropanol may be used as a suitable hydrogen donor, but other secondary alcohols may be employed for the same purpose.

It is a characteristic feature of the process of this invention that the active hydrogen-transfer (reducing) agent is produced by adsorption of a secondary alcohol, such as isopropanol, within the intracrystalline pore network of a suitable aluminosilicate, such as described above. It is another characteristics of this process that neither the crystalline aluminosilicate component nor the secondary alcohol, acts separately as a reducing agent, but that only a combination of the two is effective as a reducing system. The combination of type 13X faujasite and isopropanol is an example of a particularly powerful and selective reducing system for the conversion of saturated aldehydes and ketones into corresponding alcohols.

The process of our invention is applicable to aliphatic aldehydes with a normal or branched carbon chain, which contains from 3 to 20 carbon atoms. According to the process of this invention such $C_3$ to $C_{20}$ aldehydes can be smoothly reduced to the corresponding primary alcohols, without skeletal rearrangements and essentially without side reactions, e.g. dehydration of the alcohols produced. For example, n-valeraldehyde (n-pentanal), enanthaldehyde (n-heptanal), n-octanal, 2-ethylhexanal, and lauraldehyde (n-dodecanal) are converted into n-amyl alcohol (1-pentanol), 1-heptanol, 1-octanol, 2-ethyl-1-hexanol, and lauryl alcohol (1-dodecanol), respectively.

The process of our invention is applicable also to aliphatic ketones, containing from 3 to 20 carbon atoms and possessing either an open-chain structure or a four- to eight-membered ring system, which may be either unsubstituted or alkyl substituted. According to the process of this invention, such $C_3$ to $C_{20}$ ketones are converted to the corresponding secondary alcohols without skeletal rearrangements and practically without side reactions such as dehydration of the alcoholic products. For instance, cyclobutanone, cyclopentanone, cyclohexanone, 2-methylcyclohexanone, 3-methylcyclohexanone, 4-methylcyclohexanone, and 3-heptanone are reduced to cyclobutanol, cyclopentanol, cyclohexanol, 2-methylcyclohexanol, 3-methylcyclohexanol, 4-methylcyclohexanol, and 3-heptanol, respectively. Under identical operating conditions, the conversion of cyclic ketones to alcohols is higher than that of open-chain ketones with the same number of carbon atoms.

The process of this invention is applicable also to the reduction of unsaturated aldehydes and ketones, possessing an unconjugated double bond, e.g. citronellal. With this type of starting material, it is sometimes essential to use a specifically adapted faujasite as component of the reducing system, in order to achieve high reaction selectivity. This requirement is exemplified by the reaction of citronellal. Depending on the purpose of the process, the zeolite component in this case can be tailored either for preferential reduction of citronellal to citronellol, or for essentially exclusive reductive cyclization of citronellal to isopulegol. Control over the direction of the process by means of the zeolite component's pore size and geometry depends on the difference in environmental (steric) requirements for the above two reactions. Reductive cyclization of citronellal to isopulegol is favored by relatively large pore sizes (e.g. $\geq 9$ A), since coiling of the chain with attendant approach of the C-1 to the C-6 position in the citronellal molecule is requisite for the reaction. On the other hand, smaller pore sizes (e.g. $<8$ A), which may force the citronellal molecule to acquire an uncoiled (stretched) conformation inside the zeolite channel system, restrict the extent of cyclization and favor simple reduction to citronellol. Thus, incorporation in X-type faujasite of metal cations possessing ionic radii larger than 1.3 A produces modified channel systems which are suitable for reduction of citronellal, while with faujasites containing metal cations with small ionic radii (e.g. $<1.1$ A) cyclization of citronellal to isopulegol is strongly favored. Barium cation exchanged X-type faujasite ($Ba^{2+}$ ionic radius = 1.35 A) is an example of a suitable zeolite component in the reducing system employed in the process of this invention for conversion of citronellal to citronellol. The combination of $Ba^{2+}$- exchanged faujasite and isopropanol is an example of an efficient system for reduction of citronellal to citronellol.

The reduction or reductive cyclization processes may be performed in a flow reactor, which contains the crystalline aluminosilicate bed and which may be designed for continuous or intermittent operation, as known in the art. The aluminosilicate bed employed in the process may be either a fixed bed or a fluidized bed. Activation of the aluminosilicate may be achieved by heating in the range of 300° to 550°C under a stream of nitrogen or air. The optimal activation temperature depends on the type of aluminosilicate employed and to some extent on the nature of the substrate to be reduced. For example, an optimal temperature range of 490° to 510°C was found for activation under nitrogen of type 13X faujasite, when this zeolite is used in the reduction of cyclohexanone to cyclohexanol. The crystalline aluminosilicate bed usually shows resistance to aging under the operating conditions of this process and may be used for extended periods of time, such as several days or weeks. In some cases, however, it may be desirable to subject the bed to periodic reactivation by heating under nitrogen or air at 300° to 550°C.

One of the usual operating procedures, which offers the important advantage of a continuous process, is as follows:

A mixture of the aldehyde (or ketone) and isopropanol is introduced continuously in the reactor and contacted with the zeolite bed under a slow stream of nitrogen. Depending on the volatility of the carbonyl-containing substrate and on the operating temperature, the substrate may be either in the liquid or in the gaseous phase at the time of contact with the zeolite bed. The alcohol produced is freed from any unreacted (excess) isopropanol by means of a stripping column. The isopropanol thus recovered can be recycled with the liquid feed. Recycled isopropanol, which becomes gradually enriched in acetone produced in the hydrogen-transfer reaction, may be easily freed from this by-product by distillation. Due to the high selectivity of the reduction process, especially when saturated aldehydes and ketones are used as starting materials, the alcohols produced are usually in a high degree of purity ( >95% b.wt.).

Citronellol, b.p. 115°–117°C (14 mm), produced by the process of this invention, can be easily freed from any of the lower boiling isopulegol, b.p. 93°–94°C (14 mm), by distillation.

One of the important advantages of the process of this invention is that it can be performed at very mild temperatures, such as in the range of 25° to 250°C. Preferably, temperatures between 50° to 180°C may be employed. The process is usually conducted at about atmospheric pressure, but lower or higher pressures may be used.

The time of contact between the carbonyl-containing substrate and the aluminosilicate-isopropanol system may be varied considerably. The optimal time required depends on the nature of the substrate to be reduced, on the nature of the zeolite employed, and on the operating temperature. Generally, a liquid hourly space velocity (LHSV) in the range of 0.5 to 20 (liters of liquid feed per liter of zeolite per hour), is suitable for high conversion of the carbonyl-containing compound. However, higher or lower space velocities may be required in some cases.

Ion exchange of commercially available zeolites was performed by methods known in the art. For example, $Ba^{2+}$-exchanged X-type faujasites were prepared by contacting 13X-type molecular sieves (sodium faujasite) with a 10% solution of barium chloride in distilled water, at 82°, for periods ranging from 2 to 36 hours. The solution was replaced every two hours with a new batch of aqueous barium chloride. The ion-exchanged zeolite was washed with distilled water until free of chloride ions, filtered, dried at 120°C, and finally activated at 500°C under dry nitrogen.

The invention is illustrated by the following examples (conversions and yields are given in all cases in percent by weight). In all examples, products were identified by a combination of nmr and infrared spectroscopy, gas chromatography, and mass spectrometry. Structures of alcohols produced were confirmed by comparison with authentic reference samples. The zeolite components were in all cases in a pelletized form.

EXAMPLE 1

A batch of type 13X faujasite was preactivated at 500°C and then heated in a flow reactor to 100°C under a stream of dry nitrogen. The liquid feed, consisting of a mixture of n-valeraldehyde and isopropanol (3:10 parts by wt.) was introduced in the reactor at a constant hourly space velocity (LHSV) of 2.5 (liters of liquid feed per liter of zeolite volume per hour). A slow stream of nitrogen was maintained throughout the operation. The conversion of the aldehyde was 54% and the yield of n-amyl alcohol (1-pentanol), calculated on converted aldehyde, was 99%.

EXAMPLE 2

The aluminosilicate bed, the starting material, and the carrier gas were the same as in Example 1, but the operating temperature was set at 180°C and the LHSV employed was 5.0. The conversion of n-valeraldehyde was 94% and the yield of n-amyl alcohol, based on converted aldehyde, was 95%.

EXAMPLE 3

The aluminosilicate and the general procedure were the same as in Example 1. The starting material consisted of a mixture of enanthaldehyde (n-heptanal) and isopropanol (3:10 parts by wt.). The operating temperature was set at 100°C and the LHVS employed was 2.5. The conversion of n-heptanal was 51% and the yield of 1-heptanol, based on aldehyde converted was > 99%.

EXAMPLE 4

The faujasite bed, the starting material, and the operating conditions were the same as in Example 3, except that the temperature was set at 180°. The conversion of enanthaldehyde was 93% and the yield of 1-heptanol, based on aldehyde converted, was 98%.

EXAMPLE 5

The aluminosilicate bed and the general procedure were the same as in Example 1. The liquid feed consisted of a mixture of n-octanal and isopropanol (3:10 parts by wt.). The operating temperature was 180°, and the LHSV employed was 5.0. The conversion of n-octanal was 88% and the yield of 1-octanol, based on converted aldehyde, was 98%.

EXAMPLE 6

The aluminosilicate bed and the general procedure were the same as in Example 1. The liquid feed consisted of a mixture of 2-ethyl-1-hexanal and isopropanol (3:10 parts by wt.) and the operating temperature was 180°. The LHSV used was 5.0. The conversion of 2-ethyl-1-hexanol was 81% and the yield of 2-ethyl-1-hexanol, based on converted aldehyde, was 98%.

EXAMPLE 7

A batch of type 10X faujasite was preactivated at 400°C and then heated in a flow reactor to 180° under nitrogen. The liquid feed, consisting of n-octanol and isopropanol (3:10 parts by wt.) was introduced in the reactor at a constant LHSV of 3.5. The conversion of n-octanal was 94% and the yield of 1-octanol, based on converted aldehyde, was 98%.

EXAMPLE 8

The operating conditions and procedure were the same as in Example 7, except that the 10X faujasite bed was preactivated at 500°. The liquid feed consisted of a mixture of 2-ethyl-1-hexanal and isopropanol (1:2 parts by wt.) and the HLSV was 4.0. The conversion of the 2-ethyl-1-hexanal was 84% and the yield of 2-ethyl-1-hexanol, based on converted aldehyde, was 98%.

EXAMPLE 9

The aluminosilicate employed was type 10X faujasite, preactivated at 500°. The liquid feed consisted of a mixture of lauraldehyde (n-dodecanal) and isopropanol (3:10 parts by wt.) and the LHSV was 2.0. The operating temperature was set at 180°. Conversion of the aldehyde was 96% and the yield of lauryl alcohol (1-dodecanol), based on converted material, was 89%.

EXAMPLE 10

A batch of type 13X faujasite, used for a period of 2 weeks in runs with a variety of aldehydes as starting materials, was reactivated in situ at 400° under nitrogen. The operating temperature was set at 180°C and the liquid feed, consisting of a mixture of lauraldehyde and isopropanol (3:10 parts by wt.), was introduced in the reactor at an LHSV of 3.0. The conversion of the lauraldehyde was 91%, and the yield of lauryl alcohol, based on converted aldehyde, was 97%.

EXAMPLE 11

An aluminosilicate bed consisting of type 13X faujasite was preactivated at 500°C. A mixture of cyclobutanone and isopropanol (3:10 parts by wt.) was employed as liquid feed and the LHSV used was 2.5. The operating temperature was set at 100°. Conversion of the cyclobutanone was 55% and the yield of cyclobutanol, based on converted ketone was 72%.

EXAMPLE 12

The aluminosilicate used was type 10X faujasite, preactivated at 450°C. The liquid feed, consisting of a mixture of cyclopentanone and isopropanol (3:10 parts by wt.), was introduced in the reactor at a LHSV of 2.5 and an operating temperature of 180°. The conversion of cyclopentanone was 65% and the yield of cyclopentanol, based on converted ketone, was 99%.

EXAMPLE 13

The aluminosilicate bed used was type 13X faujasite, preactivated at 500°C, and the liquid feed consisted of a mixture of cyclohexanone and isopropanol (3:10 parts by wt.). The operating temperature was set at 100°C and the LHSV used was 2.0. The conversion of the cyclohexanone was 75% and the yield of cyclohexanol, based on converted ketone, was 99%.

EXAMPLE 14

The aluminosilicate bed, the liquid feed, and the operating conditions were the same as in Example 13, except that the temperature was set at 180°C. The conversion of the cyclohexanone was 96.5% and the yield of cyclohexanol, based on converted ketone, was 98%.

EXAMPLE 15

The aluminosilicate bed, the liquid feed, and the operating conditions were the same as in Example 13, except that the temperature was set at 70°C. The conversion of the cyclohexanone was 14%, and the yield of cyclohexanol, calculated on converted ketone, was > 99%.

EXAMPLE 16

The aluminosilicate bed employed was type 10X faujasite, preactivated at 500°C, and the liquid feed consisted of a mixture of 2-methylcyclohexanone and isopropanol (3:10 parts by wt.). The operating temperature was 180°C, and the LHSV was 3.0. The conversion of the 2-methylcyclohexanone was 76% and the yield of 2-methylcyclohexanol, based on converted ketone, was 99%.

EXAMPLE 17

The aluminosilicate bed and the operating conditions were the same as in Example 16. The liquid feed consisted of a mixture of 3-methylcyclohexanone and isopropanol (3:10 parts by wt.) The conversion of 3-methylcyclohexanone was 79%, and the yield of 3-methylcyclohexanol (a mixture of the cis- and trans-isomers), based on converted ketone, was 98%.

EXAMPLE 18

The aluminosilicate bed and the operating conditions were the same as in Example 16. The liquid feed consisted of a mixture of 4-methylcyclohexanone and isopropanol (3:10 parts by wt.). The conversion of 4-methylcyclohexanone was 94%, and the yield of 4-methylcyclohexanol (a mixture of the cis- and trans-isomers), based on converted ketone, was 98%.

EXAMPLE 19

The aluminosilicate bed used was type 13X faujasite, preactivated at 500°. The liquid feed consisted of a mixture of 3-heptanone and isopropanol (3:10 parts by wt.) and the LHSV was 2.0. The operating temperature was set at 180°C. The conversion of 3-heptanone was 16%, and the yield of 3-heptanol, based on converted ketone, was 99%.

EXAMPLE 20

The aluminosilicate bed and the operating conditions were the same as in Example 19. The liquid feed consisted of a mixture of dl-menthone and isopropanol (3:1 parts by wt.). The conversion of dl-menthone was 12%, and the yield of dl-menthol, based on converted ketone, was 98%.

EXAMPLE 21

The aluminosilicate bed and the operating conditions were the same as in Example 19. The liquid feed consisted of a mixture of 1,4-cyclohexanedione(tetrahydroquinone) and isopropanol (3:20 parts by wt.). The conversion of 1,4-cyclohexanedione was 53% and the yield of 1,4-cyclohexanediol (a mixture of the cis- and trans-isomers), based on converted diketone, was 98%.

EXAMPLE 22

A batch of barium X-type faujasite was preactivated at 500°C for 4 hours under dry nitrogen, and then heated in a flow reactor at 150°C. This was followed by pretreatment of the zeolite bed with a stream of isopropanol for a period of 10 min. The liquid feed, consisting of a mixture of citronellal and isopropanol (1:3.5 parts by wt.) was introduced in the reactor at a constant LHSV of 1.5. A slow stream of nitrogen was maintained throughout the operation. The conversion of citronellal was 92% and the yield of citronellol, based on converted aldehyde, was 53%.

EXAMPLE 23

A batch of barium X-type faujasite from a previous operation was reactivated at 390°C for 1 hour under a stream of dry nitrogen and the operating temperature was set at 150°C. The pretreatment of the zeolite bed, the composition of the liquid feed, and the LHSV were the same as in Example 22. The conversion of citronellal was 94% and the yield of cintronellol, based on converted aldehyde, was 54%.

EXAMPLE 24

The zeolite bed consisted of a batch of sodium X-type faujasite, preactivated at 500°C for 2 hours. The reaction temperature was set at 90°C and, following pretreatment of the bed with a stream of isopropanol, the liquid feed, consisting of a mixture of citronellal and isopropanol (3:10 parts by wt.) was introduced in the reactor at a constant LHSV of 2.0. A slow stream of dry nitrogen was maintained throughout the operation. The conversion of cintronellal was 57% and the yield of isopulegol, calculated on converted aldehyde, was 96%.

EXAMPLE 25

The zeolite bed used in Example 24 was reactivated at 400°C for 1 hour and the reaction temperature was set at 130°C. The pretreatment and operating procedure, the liquid feed composition, and the LHSV were the same as employed in Example 24. The conversion of citronellal was 78% and the yield of isopulegol, based on converted aldehyde, was 97%.

EXAMPLE 26

A batch of calcium X-type faujasite was activated at 480°C under dry nitrogen, and the reaction temperature was set at 70°C. The pretreatment and operating procedure, the liquid feed composition, and the LHSV were the same as in Example 24. The conversion of citronellal was 23% and the yield of isopulegol, based on converted aldehyde, was 98%.

EXAMPLE 27

A batch of Ca-exchanged mordenite, used in a previous operation, was reactivated at 390°C for 1 hour under dry nitrogen and the operating temperature was set at 150°C. The pretreatment of the zeolite bed and the liquid feed composition were the same as in Example 24. The LHSV used was 1.5. The conversion of citronellal was 84% and the yield of isopulegol, based on converted aldehyde, was 96.5%.

It is claimed that:

1. A process for the production of 3 to 20 carbon atom unsubstituted aliphatic alcohols which are saturated or contain an unconjugated double bond which comprises reducing at a temperature in the range of 25° to 250° C. and a space velocity between 0.5 and 20 liters per hour a member of the group consisting of the corresponding 3 to 20 carbon atom unsubstituted aliphatic aldehydes and ketones by means of a two component hydrogen transfer system comprising a porous crystalline aluminosilicate (molecular sieve zeolite) having an intracrystalline channel system with a pore size of 5 to 13 A and having adsorbed therein isopropanol, which compound acts within the intracrystalline channel system of the molecular sieve as a hydrogen-donor agent.

2. A process of claim 1, wherein the aldehyde or ketone is saturated.

3. A process of claim 1 wherein the molecular sieve is a member of the mordenite family of zeolites.

4. A process as claimed in claim 1, wherein the pressure is between 0.01 and 2 atmospheres.

5. A process of claim 1, wherein the aldehyde or ketone, in admixture with the secondary alcohol, is passed in a flow reactor through a bed of the aluminosilicate.

6. A process of claim 1, wherein the aluminosilicate is a $Ba^{2+}$-containing faujasite.

7. A process of claim 1, wherein the aluminosilicate is activated by heating under a stream of air or nitrogen at a temperature between 300° and 600°C.

8. A process of claim 1, wherein the liquid hourly space velocity is between 0.5 and 20 liters of liquid feed per liter of molecular sieve per hour.

9. A process of claim 1 wherein the crystalline aluminosilicate component is an X-type zeolite modified by ion exchange with a metal cation possessing an ionic radius greater than 1.3 A.

10. A process of claim 1 wherein citronellal is reduced to citronellol and the pore size of said molecular sieve is less than 8A.

11. A process of claim 1 wherein the molecular sieve is a member of the faujasite family of zeolites.

12. A process of claim 11 wherein the molecular sieve is a member of the group consisting of type 13X (sodium X-type faujasite), and type 10X (calcium X-type faujasite).

* * * * *